United States Patent [19]

Nuzzo et al.

[11] 4,384,571

[45] May 24, 1983

[54] ADJUSTABLE DIGITAL/METACARPAL SPLINT

[75] Inventors: Roy Nuzzo, Westfield, N.J.; Paul B. Gamm, Cincinnati, Ohio

[73] Assignee: Jung Corporation, Cincinnati, Ohio

[21] Appl. No.: 334,147

[22] Filed: Dec. 24, 1981

[51] Int. Cl.³ ............................................... A61F 5/10
[52] U.S. Cl. ................................... 128/77; 128/87 A
[58] Field of Search .................... 128/77, 87 R, 87 A, 128/88, 89, 90, 83

[56] References Cited

U.S. PATENT DOCUMENTS

| | | |
|---|---|---|
| 1,136,397 | 4/1915 | Bloch . |
| 1,220,476 | 3/1917 | Ujdur . |
| 1,389,741 | 9/1921 | Cotton . |
| 1,469,315 | 10/1923 | Hansard . |
| 1,817,212 | 8/1931 | Siebrandt . |
| 1,837,691 | 12/1931 | Thigpen . |
| 1,867,258 | 7/1932 | Fruehauf . |
| 2,460,652 | 2/1949 | Peterson . |
| 2,794,638 | 6/1957 | Risher et al. . |
| 2,863,449 | 12/1958 | Spencer . |
| 3,327,703 | 6/1967 | Gamm . |
| 4,103,682 | 8/1978 | Franzl . |

FOREIGN PATENT DOCUMENTS 350121 3/1922 Fed. Rep. of Germany ... 128/87 A

OTHER PUBLICATIONS

"Finger Extension Splint," Zimmer Catalogue, 1947, p. 90.
"Burnham Finger Splint," Journal Bone & Joint Surgery, Apr. 1964, p. 66.

*Primary Examiner*—John D. Yasko
*Attorney, Agent, or Firm*—Wood, Herron & Evans

[57] ABSTRACT

A digital/metacarpal splint having an elongate bone splint that is selectively positionable into splinting position with the digital bones of any one of the five fingers of a patient's hand, or with the metacarpal bones of a patient's hand. An elongate bone splint is connected to a palm plate, and the palm plate is connected to an elastic sleeve, the splint being mounted on the patient's hand and wrist through use of the elastic sleeve. The connection between bone splint and palm plate allows the bone splint to be easily and simply positioned and, thereafter, immobilized, to splint any of the hand's digital bones or metacarpal bones after the elastic sleeve, i.e., after the adjustable splint, is installed on the patient. The bone splint/palm plate connection includes a tang on one of the bone splint and the palm plate that is pivotably receivable in a tang bore formed in the other of the bone splint and the palm plate, an arcuate slot formed in one of the bone splint and the palm plate that cooperates with a slot bore formed in the other of the bone splint and the palm plate, and a fastener that passes through the slot and slot bore which is tightened when the bone splint is suitably positioned relative to the palm plate to hold those components in the desired angular position relative one to the other.

23 Claims, 6 Drawing Figures

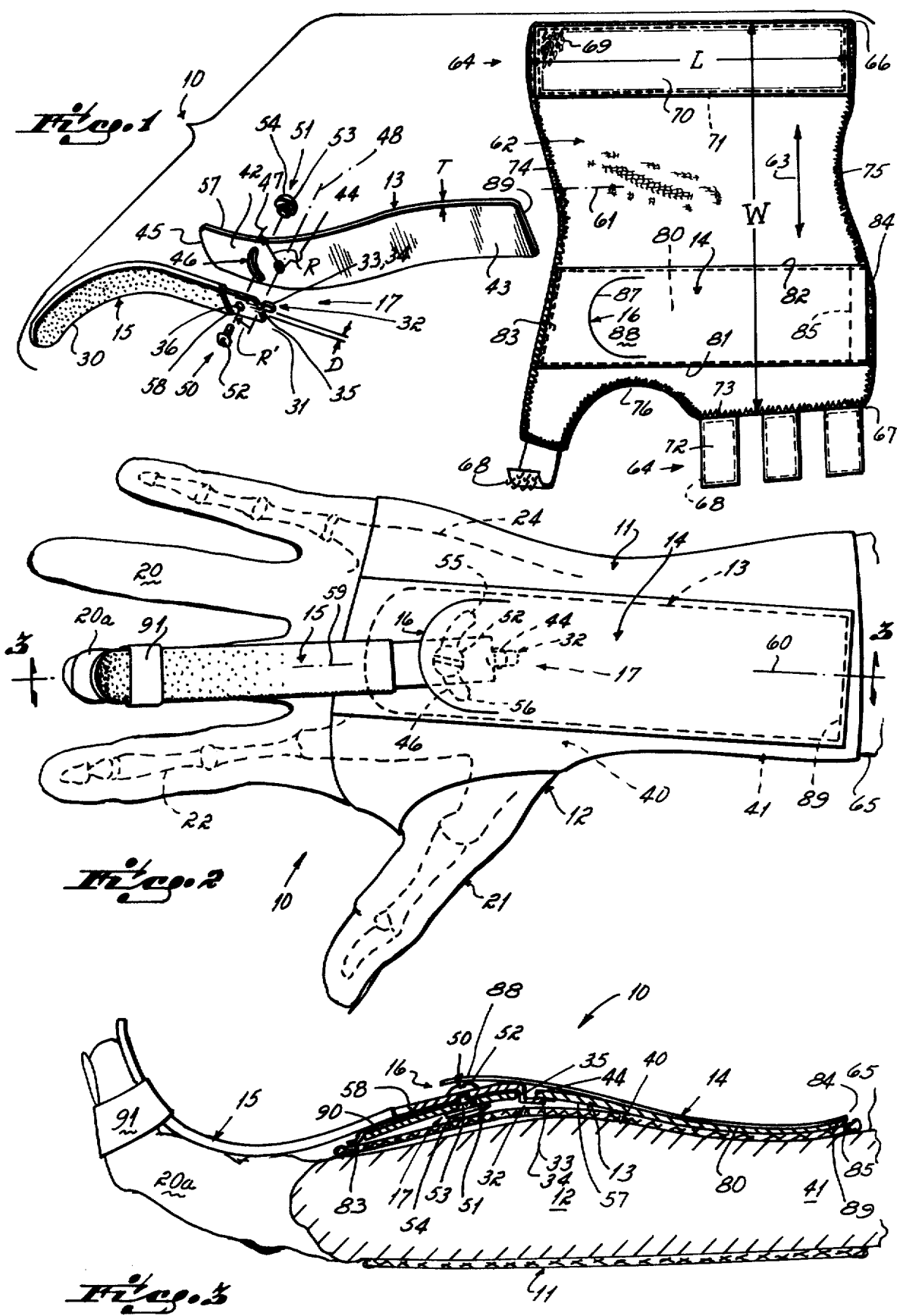

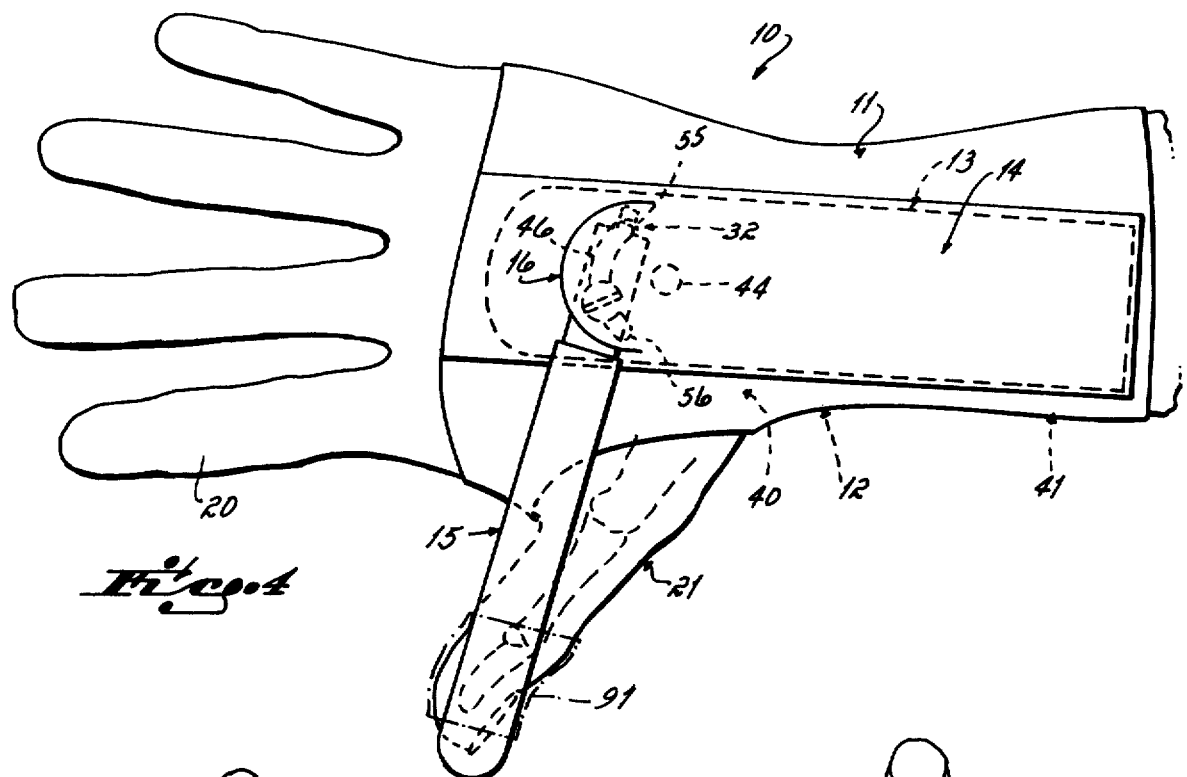
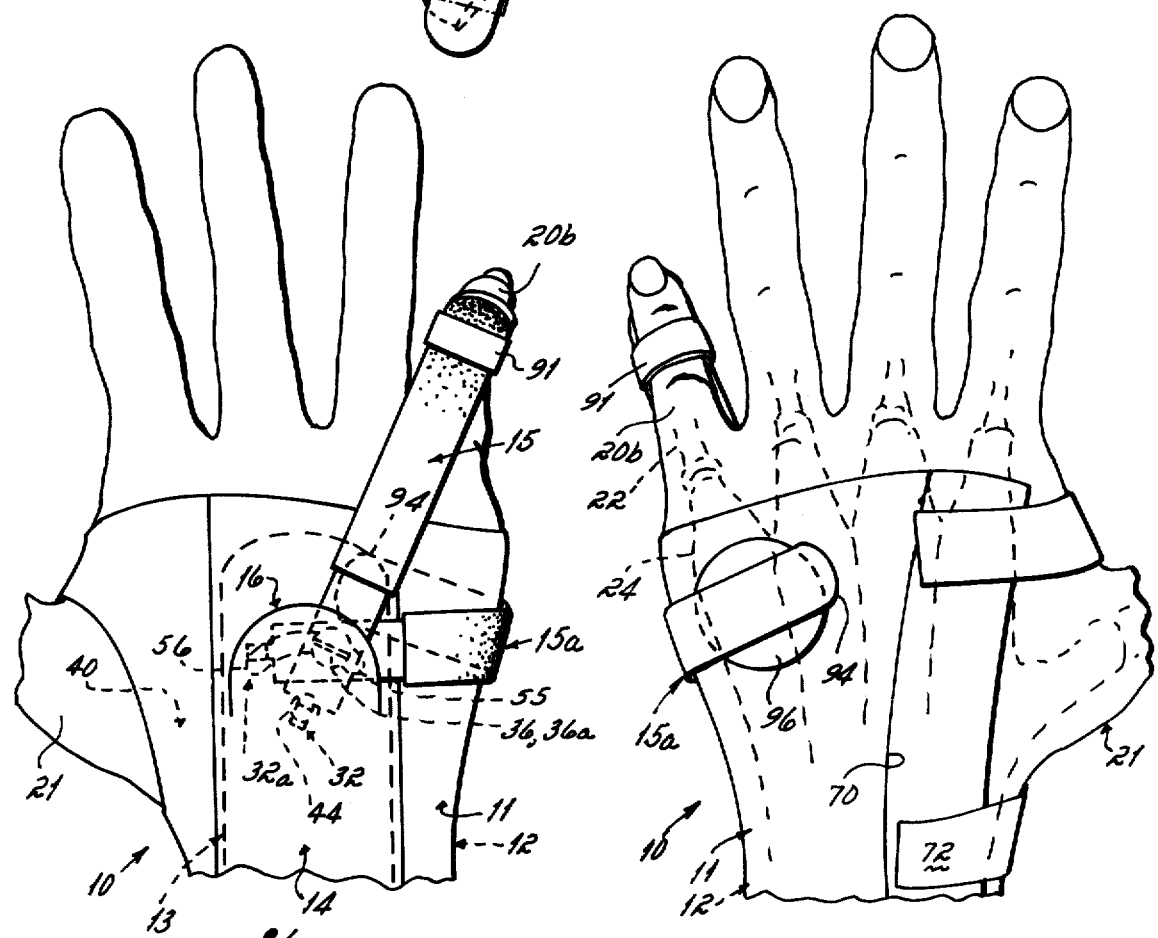

ADJUSTABLE DIGITAL/METACARPAL SPLINT

This invention relates generally to splints. More particularly, this invention relates to digital splints.

A broken digital bone is presently treated by applying a splint to the broken finger so it can be immobilized. In order to provide the necessary rigidity for the splint, one conventional technique in general use today comprises positioning an elongate bone splint against the injured finger, the splint being of a length to overlie the patient's hand, wrist and forearm region, too. A plaster cast is then applied over the patient's hand, wrist and forearm so that the splint is held in a fixed or immobile position relative to the hand. The splint is then tightly taped to the broken finger to immobilize it. In the case of a broken metacarpal bone, often referred to as a boxer's fracture, after the broken bone is set a pad is positioned over the bone on top of the hand and a plaster cast is then applied over the patient's hand, wrist and forearm. The plaster cast itself holds the newly set metacarpal bone in a fixed or immobile position relative to the hand.

The conventional cast procedure provides several problems in everyday use. First the cast procedure is time consuming, thereby reducing a physician's time that is available to serve other patients. Second, the cast procedure is usually necessarily performed only a short time after the injury occurs, and this means that the region over which the cast is applied often is still in a swollen condition. But the swelling eventually decreases, and this causes the cast to become loose. If a finger splint is used, when the cast loosens the splint will not be held sufficiently rigid to insure proper anatomical alignment of the digital bones, and if the cast is to hold metacarpal bones in place the looseness created may result in a loss of proper anatomical alignment of the metacarpal bones. In either event, a re-cast or second cast is required, and this necessitates a return visit to the physician. Conversely, and if the cast is applied before the forearm, wrist and/or hand has become completely swollen, the cast may become too tight when maximum swelling occurs. And this may necessitate removal of the original cast with replacement by another cast which, in turn, might result in the looseness problem described when the swelling subsides. Furthermore, it is often difficult to obtain an accurate x-ray of the hand area when same is encased in a plaster cast.

The disadvantages of a plaster cast for broken digital and metacarpal bones of a human hand are largely overcome in a novel adjustable digital/metacarpal splint invented by Dr. R. M. Nuzzo, which splint is disclosed in pending U.S. patent application Ser. No. 266,796, filed May 26, 1981. That splint includes an elongate bone splint which is adjustably connectable with an elongate palm plate attached to an elastic sleeve, the elastic sleeve being wrapped around the patient's hand and wrist for attaching the bone splint and palm plate to the patient's hand. The elastic sleeve is provided with adjustable fasteners so that the tightness or looseness of same may be easily adjusted on the patient's hand and wrist to compensate for any swelling while insuring that the palm plate and bone splint are securely mounted on the hand so that the splint does not slip or otherwise move out of its position as set by the physician. The elongate bone splint is connected to the palm plate by a connector structure which allows the bone splint to be positioned so as to serve any of the hand's five fingers, as well as to serve the hand's metacarpal bones. But in everyday use with patients, the connector structure for the splint illustrated in the aforementioned application has several disadvantages which are undesirable even though the basic bone splint structure and method illustrated in that application are believed to be an advance over those structures and methods heretofore known.

With the Nuzzo splint referred to above, the disadvantages are primarily in that area of the splint which allows the bone splint to be adjustably positionable relative to the palm plate, the selected position of the bone splint, of course, depending on which digital or metacarpal bones are to be immobilized by the splint. In this regard, and with the Nuzzo splint referred to above, the bone splint must be fixed in position relative to the palm plate before the splint is installed on the patient's hand, i.e., before the splint's elastic sleeve is positioned on the patient's hand. This means that if the bone splint is somewhat out of position relative to the palm plate after the splint is initially located on the patient's hand, the splint must thereafter be removed from the hand and the splint plate loosened and re-attached at the newly desired position. And this, of course, may be painful to the patient. If the out-of-position bone splint is not relocated, i.e., if the bone splint is maintained in the wrong location, and the splint kept on the patient's hand, this might cause the patient's digital or metacarpal bones to heal incorrectly. So one of the drawbacks of the Nuzzo splint, as disclosed in the above cited application, is that it has to be repeatedly installed and removed from the patient's hand until the proper alignment of the bone splint with the palm plate is achieved. Another disadvantage of the Nuzzo splint, as disclosed in the above application, is that two separate threaded fasteners are required to hold the bone splint in the desired angular relation with the palm plate. This use of two separate threaded fasteners, i.e., two separate nut and bolt fasteners, causes adjustment of the bone splint relative to the palm plate to be somewhat tedious, and also somewhat difficult. This is because one of the fasteners cannot be fully tightened, and therefor the bone splint cannot be immobily fastened to the palm plate at two locations as required, unless the bone splint and the palm plate are removed from assembly with the elastic sleeve. Such disassembly/re-assembly increases the time and tediousness of installing the splint on a patient's hand by the attending physician.

Accordingly, it has been one objective of this invention to provide an improved adjustable digital/metacarpal splint of the type having an elongated bone splint adjustably connectable to a palm plate, the palm plate being mounted on an elastic sleeve that is to be installed over the patient's hand and wrist for attaching the splint to the patient, the improved splint being structured to allow the elongated bone splint to be easily and simply positioned and re-positioned and, thereafter, immobilized, relative to the palm plate after the elastic sleeve has been fixed in place on the patient's hand and wrist.

It has been another objective of this invention to provide an improved adjustable digital/metacarpal splint of the type having an elongated bone splint adjustably connectable to a palm plate, the palm plate being mounted on an elastic sleeve that is to be installed over the patient's hand and wrist for attaching the splint to the patient, the bone splint/palm plate connection including a tang on one of the bone splint and the palm plate that is pivotably receivable in a tang bore formed in the other of the bone splint and the palm plate, an arcuate slot formed in one of the splint plate and the palm plate that cooperates with a slot bore formed in the other of the bone splint and the palm plate, and a fastener that passes through the slot and slot bore which is tightened when the splint plate is desirably positioned relative to the palm plate to hold the splint plate in place relative to the palm plate, thereby providing an improved splint that requires use of only a single fastener to hold the splint plate in a plurality of digital or metacarpal bone splint positions relative to the palm plate.

Specifically, this invention is directed to a digital/metacarpal splint having an elongate bone splint that is adjustably positionable into splinting position with the digital bones of any one of the five fingers of a patient's hand, or with the metacarpal bones of a patient's hand. The elongate bone splint is connected to a palm plate, and the palm plate is connected to an elastic sleeve, the splint being mounted on the patient's hand and wrist through use of the elastic sleeve. The connection between bone splint and palm plate allows the bone splint to be easily and simply positioned and, thereafter, immobilized, to splint any of the hand's digital bones or metacarpal bones after the elastic sleeve, i.e., after the adjustable splint, is installed on the patient. The bone splint/palm plate connection includes a tang on one of the bone splint and the palm plate that is pivotably receivable in a tang bore formed in the other of the bone splint and the palm plate, an arcuate slot formed in one of the bone splint and the palm plate that cooperates with slot bore formed in the other of the bone splint and the palm plate, and a fastener that passes through the slot and slot bore which is tightened when the bone splint is suitably positioned relative to the palm plate to hold those plates in the desired angular position relative one to the other. Preferably the bone splint mounts the tang at one end thereof, and preferably the palm plate defines the arcuate slot. In this preferred splint structure, the arcuate slot preferably is of sufficient length and width that the bone splint's tang can be received at one end of the slot, and the fastener also inserted into the slot, for connecting the two plates together. In this preferred embodiment, the bone splint can serve either the thumb bones or the metacarpal bones of the patient's hand, as well as the finger bones of all other fingers on the patient's hand.

Other objectives and advantages of this invention will be more apparent from the following detailed description taken in conjunction with the drawings in which:

FIG. 1 is an exploded view of the splint components, the elastic gauntlet being shown in the flat or unwrapped position, and the bone splint and the palm plate being shown disassembled;

FIG. 2 is a palm side view of the splint fitted on a patient's hand, and illustrating use of the splint with finger bones of one finger other than the thumb;

FIG. 3 is a sectional view taken along line 3—3 of FIG. 2;

FIG. 4 is a palm side view similar to FIG. 2, but illustrating use of the splint with finger bones of the thumb;

FIG. 5A is a palm side view similar to FIG. 2, but illustrating use of the splint with a small finger and the metacarpal bone of that finger; and FIG. 5B is a view similar to FIG. 5A but from the dorsum side of the hand.

The primary components of an adjustable digital/metacarpal splint 10 in accord with the principles of this invention are illustrated in FIG. 1. Primary components include an elastic sleeve 11 by means of which the splint is installed on a user's hand 12, a palm plate 13 receivable in pouch 14 attached to the sleeve 11, and a bone splint 15 connectable to the palm plate 13 through port 16 in the pouch 14 by a connector device 17. The various use attitudes of the splint 10 are illustrated in FIGS. 2, 4 and 5. FIG. 2 illustrates the splint 10 in a finger 20, 21 use mode which serves the digital bones 22 of the fingers 20 but not the thumb 21. FIG. 4 illustrates the splint 10 in the thumb 21 use mode which serves the thumb bones 23 only. FIGS. 5A and 5B illustrate the splint 10 in the finger 20, metacarpal bone 24 use mode which serves both the finger 20 and the metacarpal bones 24. All of these use modes are explained in greater detail below.

One of the primary components of the splint 10, as previously mentioned, is the bone splint 15. The bone splint 15 is in the nature of an extended length tongue formed from a material that, while normally rigid, is deformable only when substantial pressure is exerted thereon such as, e.g., by use of pliers. In other words, the bone splint 15 is formed from a material that will not be deformed by the muscles of a patient's hand when minimal pressure is exerted thereon. In this regard, however, and as is particularly apparent in FIGS. 3, 5A and 5B, the bone splint 15 must be deformable by a physician, e.g., through use of pliers as mentioned, so as to establish the configuration of the splint desired by the physician depending on the digital bone and/or metacarpal bone of the patient's hand with which the splint 10 is to be used. Therefore, preferably the bone splint 15 is fabricated of aluminum. Note particularly that the bone splint 15 is coated with an insulator material 30, e.g., a vinyl coating, that is impervious to water. At the inner end 31 of the bone splint 15 there is provided a downwardly and outwardly depending tang 32. The tang 32 incorporates a foot 33 at its outer end 34 and an offset section 35 between the foot and the inner end 31 of the bone splint 15. The offset section 35 is preferably of a depth D not substantially greater than the thickness T of the palm plate 13 with which it is adapted to cooperate. The bone splint 15 also includes a slot bore 36 positioned adjacent the tang end 31 of the bone splint 15. The slot bore 36 is sized to receive a threaded fastener in the form of bolt 50 as described in greater detail below.

The palm plate 13, also as shown in FIG. 1, is fabricated from material that cannot be easily bent out of shape by the muscles of a user's hand when nominal muscle pressure is exerted thereon. In this regard, and as is shown in FIG. 1, note that the palm plate 13 is initially configured in a generally curved configuration which corresponds with the curvature of a patient's hand 12 from the palm area 40 to the wrist area 41 of the hand, thereby establishing a palm section 42 and a wrist section 43 of the palm plate. As with the bone splint 15, the palm plate 13 may be fabricated from aluminum which is not easily bendable. The palm section 42 of the palm plate 13 is provided with a tang bore 44 adjacent the finger end 45, and an arcuate slot 46 is formed in the palm section between the tang bore 44 and the finger end 45 of the palm plate. Note the arcuate slot 46 is on an arc 47 of which the vertical center line 48 (which is a pivot axis as described below) of tang bore 44 constitutes the center. And note too that the radial distance R from the tang bore's center line 48 to the phantom arcuate line 47 which constitutes the center line of the arcuate slot 46 is equal to the distance R' between the tang's offset section 35 and the bone splint's slot bore 36. This spatial relationship between the tang 32 and the slot bore 36 of the bone splint 15 on the one hand, and the tang bore 44 and the arcuate slot 46 on the palm plate 13 on the other hand, allows limited pivoted movement between the bone splint 15 and the palm plate 13 when the two components are connected by connector device 17.

The connector device 17 by which the bone splint 15 is immobily secured to the palm plate 13 is also shown in FIG. 1, and is in the form of a threaded fastener comprised of bolt 50 and nut 51. The threaded bolt 50 has a head 52 adapted to receive a screw driver, and is sized to prevent the bolt from passing through slot bore 36. The specially configured nut 51 is comprised of a bushing 53 and flange 54. The nut's bushing 53, which is threaded internally, is sized to be received in the palm plate's arcuate slot 46 and to slide from end 55 to end 56 of that slot. The nut's flange 54 is sized to prevent the nut from passing through the arcuate slot 46 when it is installed therein. To assemble the bone splint 15 and the palm plate 13 in connected relation prior to insertion of same in pouch 14 of the splint's sleeve, the bone splint's tang 33 is initially inserted into the palm plate's tang bore 44, the nut 51 into the palm plate's arcuate slot 46 from the underside thereof so that the nut's flange 51 bears against the palm plate's inner face 57, and the bolt 50 inserted through the bone splint's slot bore 36 into threaded relation with the nut 51 so that the bolt's head 52 bears against the bone splint's outer face 58. The bolt 50 is subsequently tightened into the nut 51 through use of a screw driver (not shown) after the bone splint's longitudinal axis 59 has been generally aligned with the palm plate's longitudinal axis 60 by pivoting the bone splint 15 relative to the palm plate 13 on the phantom pivot axis 48 defined by the tang 32 and tang bore 44. This connects the bone splint 15 with the palm plate 13 in the preferred attitude for assembly with the sleeve's pouch 14.

The splint's elastic sleeve 11 includes a gauntlet 62, pouch 14 and gauntlet fasteners 64. The gauntlet 62, when wrapped around a user's hand 12 and wrist 41, is in the nature of a sleeve installed on the user's hand and wrist. The gauntlet 62 is fabricated from an elastic fabric which is expandable, and is the same type of fabric used in elastic bandages. This elastic fabric or material is a woven fabric in which the elastic strands extend only in a direction 63 normal to the longitudinal axis 61 of the gauntlet. The woven elastic fabric gauntlet 62 is stretchable, therefore, only in the direction 63 of the length of the elastic strands, i.e., in a direction transverse to the longitudinal axis 61 of the gauntlet, but is essentially non-stretchable in a direction parallel to the longitudinal axis of the gauntlet. The elastic fabric gauntlet 62 is of a length L sufficient to allow it, when wrapped around a user's hand 12 and wrist 41, to extend from adjacent to the hand's fingers 20 up the user's forearm 65 slightly beyond the user's wrist 41. The width W of the elastic fabric gauntlet 62 is sufficient to permit it to be wrapped completely around the user's palm 40 and wrist 41. The gauntlet 62 is restrained in tight fitting relation on the patient's hand 12 and wrist 41 by use of the gauntlet fasteners 64 positioned on opposite side edges 66, 67 of the gauntlet. The gauntlet fasteners 64 are in the form of hook 68 and loop 69 fasteners, a strip 70 of loop pile extending along one side edge 66 of the gauntlet and being sewn thereto by stitch lines 71, and a series (four are shown) of tabs 72 with hook pile each sewn along stitch line 73 to the opposite side edge 67 of the gauntlet in spaced relation one from the other between the finger edge 74 of the gauntlet and the forearm edge 75 of the gauntlet. The plurality of hook pile tabs 72 and the single loop pile strip 70 provide a definite advantage to the splint 10 in that same allow the looseness or tightness of the splint 10 on the patient's hand 12 to be adjusted without removal of same. In other words, and if it is desired to tightened the gauntlet 62 around the patient's hand 12 when all four tabs 72 are already fastened with the strip 70, only one tab need be released at a time, and thereafter re-attached in a tighter fashion, thereby permitting the gauntlet to be tightened on the patient's hand by sequentially loosening and tightening each of the four tabs. Such is desirable, and indeed may be necessary, in light of any increased or reduced swelling that may occur in the patient's hand after the splint 10 is initially installed. Note also that the side edge 67 of the gauntlet 62 is provided with a notch 76 or cutout for accommodating the thumb 21 of the patient's hand 12 when the splint 10 is installed on the patient's palm 40 and wrist 41.

The gauntlet 62 also includes a pouch 14 which is formed from a non-stretchable material, e.g., vinyl sheet, and which is sized to receive palm plate 13. The pouch 14 extends the length L of the gauntlet 62 from edge 74 to edge 75 thereof, and forms a generally rectangular pocket 80. The pouch 14 is sewn to the gauntlet's elastic fabric along opposed side edges 81, 82 and outer end edges 83 thereof, but is not sewn to the elastic fabric on the inner end edge 84 thereof. However, the non-stretchable material, e.g., vinyl sheet, from which the pouch 14 is formed is lapped over inside the pocket 80 at the forearm end 84 thereof so as to provide a flap 85 which normally is directed inwardly. Note particularly that the pouch defines an access port 16 adjacent the outer end thereof for the bone splint 15, the access port being established by a slit 87 of generally arcuate configuration and extending from one side edge 81 to the other side edge 82 of the pouch 14. The arcuate slit 87 cooperates to define a flap 88 for the port 16 so formed in the pouch, thereby providing access to the threaded fastener 50, 51 when the bone splint 15 and palm plate are assembled with the gauntlet 62.

To assemble the pre-assembled bone splint 15 and palm plate 13 in operative assembly within the gauntlet's pouch 14, the bone splint is initially introduced into the pocket 80 from the open end 84 thereof and is pushed through the pocket and then out through the port 16 in the pouch defined by the pouch's flap 88. Of course, the palm plate 13 is also introduced similarly into the pouch's pocket 80 since it is connected to the bone splint, but it is retained completely within the pouch. Since the palm plate 13 is of a length substantially equal to the length of the pouch's pocket 80, the inwardly turned flap 85 on the open end 84 of the pouch 14 serves as a seat against which the wrist end 89 of the palm plate is received to prevent the palm plate from tending to back out of the pouch after it has been inserted therein.

Use of the adjustable splint 10 for any finger 20 except the thumb 21 is illustrated in FIGS. 2 and 3. As shown therein, the splint's gauntlet 62 is initially wrapped somewhat tightly around the patient's palm 40 and wrist 41 with same being securely fastened in place by use of the hook and loop fasteners 64. The advantage of the elastic fabric from which the gauntlet is formed is that same may be stretched as loosely or as tightly around the patient's palm 40 and wrist 41 as is desired by the physician in order to achieve a taut or tight fit so that the palm plate 13 is held immobile relative to the user's hand. In this preliminary position, the bone splint 15 is then finally formed into that desired curved configuration desired by the attending physician. The position of the bone splint 15 relative to the four fingers 20, of course, depends on which of the four fingers has broken digital bones to be served by the splint. Assuming it is the middle finger 20a as shown in FIG. 2, and since the bolt 50 is not in fully tightened position relative to the nut 51, the bone split can be pivoted on pivot axis 48 between outer pivot limits defined by ends 55, 56 of arcuate slot 46 until the final desired position is achieved. Once the final desired position is achieved, of course, the bolt 50 is tightened against the nut 51 for tightening the bone splint 15 against the palm plate 13, the bolt being easily accessible to a screw driver simply by lifting up flap 88 of pouch 14. This, of course, immobily holds the bone splint 15 in the desired position relative to the finger 20a. Note particularly that the bone splint 15 can be easily positioned and re-positioned by the attending physician, until the desired final position is achieved, without the necessity to remove the splint 10 from the patient's hand 40. In other words, and in order to finalize the preferred position of the bone splint 15 relative to the patient's hand 40, it is not necessary to remove the splint 10 from the patient's hand once it has been initially installed since the threaded fastener 50, 51 easily slides in arcuate slot 46. This, of course, is quite desirable in that periodic removal and replacement of the splint 10 could be painful to the patient. And, importantly, since only a single threaded fastener 50, 51 is used, the flap 88 in the pouch 14 which allows the bone splint 15 to pivot relative to the palm plate 13 can be of dimensions sufficient only to permit that pivoting action, i.e., it need not be of sufficient depth to allow adjustment of the tang connection at tang 32/tang bore 46 since no threaded connector is used at that location as is used in the prior Nuzzo splint. Further, and when the bone splint 15 is tightened down against the palm plate 13, note that the finger end portion 90 of the material which defines the pouch 14 is trapped between the bone splint and the palm plate, see FIG. 3. This is an important aspect for, in effect, it thereby directly connects the bone splint 15 and palm plate 13 with the gauntlet 62 itself since the pouch 14 is sewn to that gauntlet, thereby tending to immobilize the palm plate and bone splint relative to the gauntlet. And of course this is quite desirable for the bone splint 15, palm plate 13 and gauntlet 62 all working together are, in effect, made a part of the patient's hand with no relative movement between any of those parts relative to the patient's hand. This reduces the possibility of the finger 20, a moving relative to the hand 40, after it is taped by tape 91 to the bone splint 15 because to allow such movement might cause pain in the patient's finger and/or hand. Note also, and as shown in FIG. 3, that when the bone splint 15 is immobily connected relative to the palm plate 13 that the foot 33 of the bone splint's tang 32 in effect lies flush against the palm plate's inner face 57 and, therefore, flush against the patient's palm 40. This is desirable because it tends to minimize the discomfort to the patient since no sharp object is projecting into the patient's palm at this location.

In this regard, the tang 32 requires less of an extension or offset depth D from the bone splint 15 to the tang's foot 33 in order to achieve a connection relative to the palm plate 13 than would be the case with a threaded fastener of the bolt and nut type. In other words, the extension depth D of the tang 32 is not substantially greater than the thickness T of the palm plate 13, and the tang foot 33 is disposed flush against the underside 57 of the palm plate 13 when the bone splint 15 is installed therewith, thereby providing minimal discomfort to the patient's palm 40 brought about by the protuberance at that connect location.

When it is desired to use the splint plate 15 with the thumb 21, the arrangement shown in FIG. 4 may be established after the gauntlet 62 is attached to the patient's hand and wrist. After that initial attachment occurs, and assuming the bone splint 15 is attached with the palm plate 13 in the configuration shown in FIG. 2, the threaded bolt 50 need merely be removed from the bolt 51, the bone splint's tang 32 removed from the palm plate's tang bore 44, and the bone splint 15 re-oriented thereafter as shown in FIG. 4. In this thumb orientation the bone splint's tang 32 is received in the palm plate's arcuate slot 46, fits under the palm plate, and abuts the outer end 56 of the arcuate slot relative to the patient's thumb 21. Subsequently the nut 51 is in arcuate slot 46 toward end 57 (the nut cannot escape the slot because it is trapped therein), and the bolt 50 passed through the bone splint's slot bore 36 and screwed into connection relation with the nut. Again, and as in the case in the FIG. 2 use mode, the bone splint 15 is retained in fixed relation with palm plate 13 and gauntlet 62 by a single adjustable fastener 50, 51, and by the bone splint's tang 32 cooperating with the palm plate 13. When the final thumb position of the bone splint has been selected by the physician, the fastener 50, 51 is tightened down and the thumb 21 wrapped with adhesive tape or the like around the bone splint 15 so as to hold it in immobilized fashion. Note particularly in both this thumb use mode that only a single fastener 50, 51 is required, the tang's foot 33 extending under and generally parallel to the palm plate 13.

Similar to the FIG. 4 installation and adjustment mode of the splint for the thumb 21, the FIGS. 5A and 5B installation mode permits use of the splint with one or more broken metacarpal bones. In this metacarpal bone mode, and after the gauntlet 62 is installed on the patient's hand and wrist, and assuming the splint plate is oriented as shown in FIG. 2 during that initial installation, the bolt 50 is removed from the nut 51, thereby allowing the bone splint's tang 32 to be lifted out of the palm plate's tang bore 44, i.e., thereby allowing the bone splint to be disconnected from the palm plate 13. While removed from assembly with the palm plate 13, the bone splint 15 can be conformed around the dorsum side of the hand 40 so that free end 94 of bone splint 15 will overlie the metacarpal bones 24 on the dorsum side of the hand after being reconnected with the palm plate 13. The bone splint 15 is then re-oriented as shown in FIG. 5A with the bone splint's tang abutting the thumb end 57 of the arcuate slot 46, and the tang 32 being received in the arcuate slot against end 56 thereof. The threaded bolt 50 is then reconnected with the nut 51 through the bone splint's slot bore 36 and through the arcuate slot 46 as shown in FIG. 5A to restrain and immobily fix the bone splint to the palm plate. In this position, and with, for example, a foam pad 96 interposed between the splint plate's tongue 94 and the hand's dorsum side as shown in FIG. 5B, the bone splint will exert the desired pressure on any one or more of the metacarpal bones 24 for restraining those bones in that position set by the physician. Of course since it is unlikely the physician will curve or configure the bone splint 15 exactly as required on the first effort, it is important to note that the bone splint 15 can be easily disconnected and reconnected to the palm plate 13 as often as necessary by the physician until the final desired configuration is obtained without removing the gauntlet from the patient's head and wrist.

It is also important to note that the adjustable splint 10 of this invention can make use of two bone splints 15, 15a in operative assembly with the palm plate 13. For example, it might be necessary to splint the digital bones of first finger 20b and the metacarpal bone associated with that first finger. In this event, and as also shown in FIGS. 5A and 5B, a second bone splint 15a can be connected with palm plate 13 in the manner as shown and described in connection with the FIGS. 2 and 3 use mode. Note particularly that even in this dual bone splint 15, 15a use mode, that only a single threaded fastener 50, 51 is required since the slot bores 36, 36a of bone splints 15, 15a both are aligned one with the other, as well as with arcuate slot 46, in order to accomplish immobile assembly of those bone splints with the palm plate 13.

Having described in detail the preferred embodiment of our invention, what we desire to claim and protect by Letters Patent is:

1. An adjustable digital/metacarpal splint for a hand, said splint comprising
    an elongate bone splint, said bone splint including a tang that extends from one end thereof and a slot bore located adjacent said one end,
    a palm plate configured to substantially correspond to the contour of a user's hand between the wrist and palm thereof, said palm plate including a tang bore at the finger end thereof, and an arcuate slot located between said tang bore and said finger end, said bone splint's tang being received in said palm plate's tang bore and said bone splint's slot bore overlying said palm plate's arcuate slot when said bone splint and said palm plate are assembled one with the other,
    a splint fastener that cooperates with said bone splint's slot bore and with said palm plate's arcuate slot for holding said bone splint and palm plate in immobile assembled position relative one to the other, said palm plate's arcuate slot cooperating with said fastener when said fastener is loosened but not removed from operative assembly with said splint to permit said bone splint to pivot on an axis defined by said tang, between limits defined by the ends of said arcuate slot, and
    a sleeve defined at least in part by an elastic fabric material, said palm plate being connected to said sleeve, and said sleeve being positionable around a user's hand and wrist for installing said splint on a user's hand.

2. An adjustable digital/metacarpal splint as set forth in claim 1, said tang comprising
    a foot configured to be positioned on one side of said palm plate when said bone splint is positioned on the other side of said palm plate, said foot cooperating with said sleeve and said palm plate to prevent inadvertent withdrawal of said tang from said tang bore when said bone splint is assembled with said palm plate.

3. An adjustable digital/metacarpal splint as set forth in claim 1, said arcuate slot being sized to receive said tang, as well as to be in registry with said slot bore, when in the thumb bone use mode, said bone splint being angled relative to said palm plate for use with the user's thumb when in said thumb bone use mode.

4. An adjustable digital/metacarpal splint as set forth in claim 1, said arcuate slot being sized to receive said tang, as well as to be in registry with said slot bore, when said bone splint is in the metacarpal bone use mode, said bone splint being angled relative to said palm plate in said metacarpal bone use mode to permit said bone splint to be curved around from the palm side of a user's hand to overlie the dorsum side of a user's hand.

5. An adjustable digital/metacarpal splint as set forth in claim 4, said splint comprising
    two elongate bone splints, one being positioned in a finger bone use mode and the other being positioned in a metacarpal bone use mode, said tang of one bone splint being received in said arcuate slot and said tang of said other bone splint being received in said tang bore.

6. An adjustable digital/metacarpal splint as set forth in claim 5, said splint comprising
    a single splint fastener, the slot bores of said two bone splints being aligned one with another and with said arcuate slot so that only a single fastener is required to connect both said bone splints in immobile assembly with said palm plate.

7. An adjustable digital/metacarpal splint as set forth in claim 1, said splint comprising
    a pouch fixed to said sleeve on the palm side of said sleeve, said palm plate being received in said pouch.

8. An adjustable digital/metacarpal splint as set forth in claim 7, said pouch comprising
    an opening through which said bone splint extends, and
    a closure flap adapted to generally close said opening, said closure flap being sized to permit access to said splint fastener.

9. An adjustable digital/metacarpal splint as set forth in claim 7, at least a portion of said pouch being positioned between said bone splint and said palm plate, said pouch thereby being trapped between said bone splint and said palm plate when said splint fastener is tightened for immobilizing said bone splint relative to said palm plate, thereby aiding in prevention of movement of said palm plate relative to said sleeve during use of said splint.

10. An adjustable digital/metacarpal splint as set forth in claim 1, said splint fastener comprising
    a threaded fastener.

11. An adjustable digital/metacarpal splint as set forth in claim 10, said threaded fastener comprising
    a bolt and a nut, the head of said bolt being positioned to bear against said bone splint and said nut being positioned to bear against said palm plate.

12. An adjustable digital/metacarpal splint as set forth in claim 11, said nut comprising
    a bushing and a flange, said bushing being threaded to receive said bolt, said bushing being positioned within said arcuate slot and being sized to permit sliding of said bushing from one end of said slot to the other, said flange being sized to prevent said bushing from passing through said arcuate slot and being positioned between said palm plate and said sleeve, said palm plate and said sleeve thereby trapping said nut within said arcuate slot to prevent said nut from becoming inadvertently removed from assembly with said splint.

13. An adjustable digital/metacarpal splint as set forth in claim 1, said sleeve comprising
 a gauntlet having opposite side edges disposed generally parallel to the longitudinal axis of a user's hand and arm when said splint is installed, and
 gauntlet fasteners connected to said opposed side edges, said gauntlet fasteners being adapted to hold said sleeve tight about a user's hand and wrist when said splint is installed.

14. An adjustable digital/metacarpal splint as set forth in claim 13, said gauntlet fasteners comprising
 hook and loop fasteners, said hook and loop fasteners being partially carried on each of said opposed side edges.

15. An adjustable digital/metacarpal splint as set forth in claim 14, said hook and loop fasteners comprising
 a plurality of straps carrying the others of said hooks and loops on the other side edges of said sleeve, said plural straps permitting said gauntlet to be adjusted along its length without unloosening all fasteners simultaneously.

16. an adjustable digital/metacarpal splint for a hand, said splint comprising
 an elongate bone splint, said bone splint being bendable into a desired configuration for providing desired support of a user's digital or metacarpal bones,
 a palm plate configured to substantially correspond to the contour of a user's hand between the wrist and palm thereof,
 connector structure by which said bone splint is adjustably connectable to said palm plate, said connector structure comprising
  a tang on one of said bone splint and said palm plate that is pivotably receivable in a tang bore formed in the other of said bone splint and said palm plate,
  an arcuate slot formed in one of said bone splint and said palm plate, and
  a splint fastener connected to that one of said bone splint and said palm plate in which said arcuate slot is not formed, said fastener passing through said arcuate slot when said bone splint is positioned as desired relative to said palm plate to hold said bone splint and palm plate in that desired position relative on to the other, and
 a sleeve defined at least in part by an elastic fabric material, said palm plate being connected to said sleeve, and said sleeve being positionable around a user's hand and wrist for installing said splint on a user's hand.

17. An adjustable digital/metacarpal splint as set forth in claim 16, said arcuate slot cooperating with said fastener when said fastener is loosened but not removed from operative assembly with said bone splint to permit said bone splint to pivot on an axis defined by said tang and said tang bore between limits defined by the ends of said arcuate slot.

18. An adjustable digital/metacarpal splint as set forth in claim 16, said splint comprising
 a slot bore defined in that one of said bone splint and said palm plate in which said arcuate slot is not formed, said tang being received in said tang bore and said slot bore overlying said arcuate slot when said bone splint and said palm plate are assembled one with the other.

19. An adjustable digital/metacarpal splint as set forth in claim 18, said tang extending from one end of said bone splint, said slot bore being located adjacent said one end of said bone splint, said tang bore being located at the finger end of said palm plate, and said arcuate slot being located in said palm plate between said tang bore and said finger end.

20. An adjustable digital/metacarpal splint as set forth in claim 16, said arcuate slot being sized to receive said tang, as well as to receive said fastener, when in the thumb bone use mode, said bone splint being angled relative to said palm plate for use with the user's thumb when in said thumb bone use mode.

21. An adjustable digital/metacarpal splint as set forth in claim 16, said arcuate slot being sized to receive said tang, as well as to receive said fastener, when said bone splint is in the metacarpal bone use mode, said bone splint being angled relative to said palm plate in said metacarpal bone use mode to permit said bone splint to be curved around from the palm side of a user's hand to overlie the dorsum side of a user's hand.

22. An adjustable digital/metacarpal splint as set forth in claim 21, said splint comprising
 two elongate bone splints, one being positioned in a finger bone use mode and the other being positioned in a metacarpal bone use mode, said tang of one bone splint being received in said arcuate slot and said tang of said other bone splint being received in said tang bore.

23. An adjustable digital/metacarpal splint as set forth in claim 22, said splint comprising
 a single splint fastener to connect both said bone splints in immobile assembly with said palm plate.

* * * * *